(12) United States Patent
Voigt et al.

(10) Patent No.: US 9,638,777 B2
(45) Date of Patent: May 2, 2017

(54) ELECTRIC PROPERTIES TOMOGRAPHY IMAGING METHOD AND SYSTEM

(75) Inventors: Tobias Ratko Voigt, London (GB); Ulrich Katscher, Norderstedt (DE); Thomas Hendrik Rozijn, Eindhoven (NL); Paul Royston Harvey, Eindhoven (NL); Hanno Homann, Hamburg (DE); Christian Findeklee, Norderstedt (DE); Eberhard Sebastian Hansis, Menlo Park, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1323 days.

(21) Appl. No.: 13/522,367

(22) PCT Filed: Jan. 13, 2011

(86) PCT No.: PCT/IB2011/050146
§ 371 (c)(1),
(2), (4) Date: Aug. 27, 2012

(87) PCT Pub. No.: WO2011/086512
PCT Pub. Date: Jul. 21, 2011

(65) Prior Publication Data
US 2012/0306493 A1 Dec. 6, 2012

(30) Foreign Application Priority Data

Jan. 18, 2010 (EP) .................................... 10150979

(51) Int. Cl.
*G01R 33/54* (2006.01)
*G01R 33/341* (2006.01)
(Continued)

(52) U.S. Cl.
CPC .............. *G01R 33/48* (2013.01); *A61B 5/055* (2013.01); *A61B 5/0536* (2013.01); *G01R 33/246* (2013.01); *G01R 33/443* (2013.01)

(58) Field of Classification Search
CPC .... A61B 5/055; A61B 5/0536; G01R 33/246; G01R 33/443; G01R 33/48
(Continued)

(56) References Cited

U.S. PATENT DOCUMENTS

| | | | |
|---|---|---|---|
| 6,397,095 B1 | 5/2002 | Eyuboglu et al. | |
| 7,511,492 B2 | 3/2009 | Sodikson et al. | |

(Continued)

FOREIGN PATENT DOCUMENTS

| | | |
|---|---|---|
| WO | 2007017779 A2 | 2/2007 |
| WO | 2009118688 A1 | 10/2009 |

OTHER PUBLICATIONS

Bulumulla, S. B., et al.; Direct calculation of tissue electrical parameters from B1 maps; 2009; Proc. Intl. Soc. Mag. Reson. Med.; 17:3043.

(Continued)

*Primary Examiner* — Melissa Koval
*Assistant Examiner* — Rishi Patel

(57) ABSTRACT

A magnetic resonance method of electric properties tomography imaging of an object includes applying an excitation RF field to the object via a coil at a first spatial coil position (402), acquiring resulting magnetic resonance signals via a receiving channel from the object, determining from the acquired magnetic resonance signals a first phase distribution and a first amplitude of a given magnetic field component of the excitation RF field of the coil at the first coil position (402), repeating these steps with a coil at a second different spatial coil position (404), to obtain a second phase distribution, determining a phase difference between the first (Continued)

and second phase distribution, determining a first and a second complex permittivity of the object, the first complex permittivity comprising the first amplitude of the given magnetic field component and the second complex permittivity comprising the second amplitude of the given magnetic field component and the phase difference, equating the first complex permittivity and the second complex permittivity for receiving a final equation and determining from the final equation a phase of the given magnetic field component for the first coil position (402).

11 Claims, 5 Drawing Sheets

(51) Int. Cl.
    *G01R 33/48*     (2006.01)
    *A61B 5/053*     (2006.01)
    *A61B 5/055*     (2006.01)
    *G01R 33/24*     (2006.01)
    *G01R 33/44*     (2006.01)

(58) Field of Classification Search
    USPC .................. 324/307, 309, 318, 322; 600/420
    See application file for complete search history.

(56) References Cited

U.S. PATENT DOCUMENTS

2009/0102480 A1     4/2009     Katscher et al.
2012/0139541 A1*   6/2012   Weiss ................... G01R 33/583
                                                       324/318
2014/0239951 A1*   8/2014   Van Lier ................ A61B 5/053
                                                        324/309

OTHER PUBLICATIONS

Graesslin, I., et al.; Safety considerations concerning SAR during RF amplifier malfunctions in parallel transmission; 2006; ISMRM; 14:2041.

Katscher, U., et al.; Electric Properties Tomography (EPT) via MRI; 2006; Proc. Intl. Soc. Mag. Reson. Med.; 14:3037.

Katscher, U., et al.; In vivo determination of electric conductivity and permittivity using a standard MR system; 2007; IFMBE Proceedings 17; pp. 508-511.

Katscher, U., et al.; Determination of Electric Conductivity and Local SAR via B1 Mapping; 2009; IEEE Trans. on Medical Imaging; 28(9)1365-1374.

Voigt, T., et al.; Simultaneous B1 and T1 mapping based on modified "Actual Flip-angle Imaging"; 2009; Proc. Intl. Soc. Mag. Reson. Med.; 17:4543.

Wren, H.; Non-invasive Quantitative Mapping of Conductivity and Dielectric Distributions Using the RF Wave Propagation Effects in High Field MRI; 2003; Proceedings of the SPIE Intl. Soc. for Optical Engineering; vol. 5030; pp. 471-477.

Yarnykh, V. L.; Actual Flip-Angle Imaging in the Pulsed Steady State: A Method for Rapid Three-Dimensional Mapping of the Transmitted Radiofrequency Field; 2007; MRM; 57:192-200.

Zhang, X., et al.; Magnetic Resonance Electric Property Imaging of Brain Tissues; 2009; IEEE Engineering in Medicine and Biology Society; pp. 4432-4435.

\* cited by examiner

ELECTRIC PROPERTIES TOMOGRAPHY IMAGING METHOD AND SYSTEM

FIELD OF THE INVENTION

The present invention relates to a magnetic resonance method of electric properties tomography imaging of an object, a computer program product, as well as a magnetic resonance system for performing electric properties tomography imaging of an object.

Image forming MR (magnetic resonance) methods which utilize the interaction between magnetic field and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

BACKGROUND OF THE INVENTION

According to the MR method in general, the body of a patient or in general an object has to be arranged in a strong, uniform magnetic field whose direction at the same time defines an axis (normally the z-axis) of the coordinate system on which the measurement is based. The magnetic field produces different energy levels for the individual nuclear spins independent of the magnetic field strength which can be excited (spin resonance) by application of an electromagnetic alternating field (RF field) of defined frequency (so called Larmor frequency, or MR frequency). From a microscopic point of view, the distribution of the individual nuclear spins produces an overall magnetization which can be deflected out of the state of equilibrium by application of an electromagnetic pulse of appropriate frequency (RF pulse) while the magnetic field extends perpendicular to the z-axis, also referred to as longitudinal axis, so that the magnetization performs a precessional motion about the z-axis. The precessional motion describes the surface of a cone whose angle of aperture is referred to as flip angle. The magnitude of the flip angle is dependent on the strength and the duration of the applied electromagnetic pulse. In the case of the so called 90 degree pulse, the spins are deflected from the z-axis to the transverse plane (flip angle 90 degrees).

After termination of the RF pulse, the magnetization relaxes back to the original state of equilibrium, in which the magnetization in the z-direction is built up again with a first time constant T1 (spin-lattice or longitudinal relaxation time), and the magnetization in the direction perpendicular to the z-direction relaxes with a second time constant T2 (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example a 90 degree pulse, by a transition of the nuclear spins induced by local magnetic field inhomogeneities from an ordered state with the same phase to a state in which all phase angles are uniformly distributed (de-phasing). The de-phasing can be compensated by means of a refocusing pulse, for example 180 degree pulse. This produces an echo signal (spin echo) in the receiving coils.

In order to realize spatial resolution in the body, linear magnetic field gradients extending along the three main axes are superimposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image by means of Fourier transformation.

Electric properties tomography (EPT) is a recently developed approach to determine electric conductivity σ, permittivity ε and local SAR (specific absorption rate) in vivo using standard MR systems. For EPT, the spatial components of the magnetic field of the transmission/reception RF coil involved are measured and post-processed. One substantial advantage of EPT compared to the well known electric impedance tomography (EIT) or MR-EIT is that EPT does not apply any external currents to the patients or objects to be examined. Optimally, all three spatial components of the RF coil's magnetic field are measured and post-processed. Typically, the spatial amplitude distribution of one of these three components can be measured exactly, namely the positive circularly polarized component $H^+$. However, determination of the two other components, namely the negative circularly polarized magnetic field component $H^-$ and $H_z$ are rather difficult to determine. Furthermore, MR imaging always yields a mixture of the spatial phase distributions τ and ρ, corresponding to the transmit sensitivity $H^+$ and the receive sensitivity $H^-$, respectively.

An electric impedance imaging system to explore the electrical conductivity and permittivity distribution of an object is known for example from WO 2007/017779.

SUMMARY OF THE INVENTION

It is an object of the present invention to provide an improved magnetic resonance system for performing electric properties tomography imaging of an object, an improved magnetic resonance method of electric properties tomography imaging of an object, as well as an improved computer program product.

In accordance with the invention, a magnetic resonance method of electric properties tomography imaging of an object is disclosed. The method comprises applying an excitation RF field to the object via a coil at a first spatial coil position, acquiring resulting magnetic resonance signals via a receiving channel from the object, determining from the acquired magnetic resonance signals a first phase distribution and a first amplitude of a given magnetic field component of the excitation RF field of the coil at a first coil position. The method further comprises applying an excitation RF field to the object via a coil at a second spatial coil position, wherein the second spatial coil position is different from the first spatial coil position, acquiring resulting magnetic resonance signals via the receiving channel from the object, determining from the acquired magnetic resonance signals a second phase distribution and a second amplitude of the given magnetic field component of the excitation RF field of the coil at a second coil position.

Multiple coil positions can be realized for example by changing the position of a single coil sequentially, or by sequentially using different elements of an array of independent TX (transmit) channels.

Further, a phase difference between the first and second phase distribution is determined and a first and second complex permittivity of the object is determined, wherein the first complex permittivity comprises the first amplitude of the given magnetic field component and a second complex permittivity comprises the second amplitude of the given magnetic field component and the phase difference. Finally, the first complex permittivity and the second complex permittivity are equated for receiving a final equation. From the final equation, a phase of the given magnetic field component for the first coil position is determined.

It has to be noted here, that the application of the excitation RF field to the object via the coil at the first and second spatial coil position is performed preferably subsequently in time and thus not simultaneously in time.

Embodiments of the present invention have the advantage, that the spatial phase distribution of the given magnetic field component of the excitation RF field of the coil at the first coil position can be determined exactly. Consequently, when calculating a complex permittivity map of an object this calculation does not rely anymore on any assumptions and approximations regarding the phase distribution as known from the prior art. Therefore, the complex permittivity of the object can be determined at higher accuracy.

In accordance with an embodiment of the invention, the method further comprises employing in the final equation the phase of the given magnetic field component for the first coil position as a parametrizable function, for example as a polynomial. This has the advantage, that instead of a pixel-wise determination of the phase of the given magnetic field component for the first coil position from the final equation it is assumed that the phase can be approximated by a polynomial, such that a determination of the phase is limited to finding a predetermined set of coefficients of the polynomial which drastically speeds up the phase determination process.

In accordance with a further embodiment of the invention, the given magnetic field component is a positive circularly polarized magnetic field component of the excitation RF field at the first coil position, wherein the method further comprises determining a negative circularly polarized magnetic field component at the first coil position, wherein said determination of the negative circularly polarized magnetic field component comprises applying an excitation RF field to the object via the coil at the first coil position, acquiring resulting magnetic resonance signals via said coil from the object and determining from the acquired magnetic resonance signals a third phase distribution of the positive circularly polarized magnetic field component of the excitation RF field.

Further, from the third phase distribution and the phase of the positive circularly polarized magnetic field component of the excitation RF field at the first coil position the phase of the negative circularly polarized magnetic field component at the first coil position is determined. This is followed by determination of a third complex permittivity of the object, said third complex permittivity comprising the phase of the negative circularly polarized magnetic field component at the first coil position. Finally, the first complex permittivity and the third complex permittivity are equated for receiving an equation and from said equation for the first coil position an amplitude of the negative circularly polarized magnetic field is determined from said equation.

This has the advantage, that in a highly accurate manner all three spatial magnetic field components can be determined. For example,*after determination of $H^+$ and $H^-$ the corresponding Cartesian components can be calculated by the definition of the circularly polarized components. The final missing component $H_z$ can then be determined via the magnetic Gauss law. Consequently now amplitude and phase of all three spatial magnetic field components are determined, enabling a very reliable determination of local SAR.

It has to be noted, that for determining the amplitude of the negative circularly polarized magnetic field, in the respective equation also the amplitude of the magnetic field component may be employed as a polynomial to speed up the calculation process.

The above mentioned method shall be described in a more detailed way in the following:

State of the art reconstruction of $\underline{\epsilon}$ (published for example in IEEE Transactions on Medical Imaging, Vol. 28, No. 9, pp. 1365ff, September 2009) uses only the positive circularly polarized field component $\underline{H}^+$, which can be measured via standard B1 mapping (see, e.g., Yarnykh V L. Actual flip-angle imaging in the pulsed steady state: a method for rapid three-dimensional mapping of the transmitted radiofrequency field. MRM 57 (2007) 192-200). However, such B1 mapping sequences acquire only the spatial amplitude distribution of $\underline{H}^+$, but not its spatial phase distribution $\tau$. Taking RF shimming as prominent example where B1 mapping is required, the spatial phase distribution $\phi$ of a standard MR image is taken instead. This phase distribution, however, is the superposition $\phi = \tau + \rho$ of the phase $\tau$ of the transmit field $\underline{H}^+$ and the phase $\rho$ of the receive field $\underline{H}^-$. This contamination of $\tau$ is irrelevant for RF shimming, but not for EPT due to the applied calculus operations.

The phase distribution $\phi_{uv}$ of a standard MR image using transmit channel u and receive channel v is given by $$\phi_{uv} = \tau_u + \rho_v \quad (1)$$

From two separate measurements with different transmit channels (first and second coil position) but same receive channels, the phase difference between the first and second phase distribution can be obtained as $$\delta_{uv} = \phi_{uv} - \phi_{vv} = (\tau_u + \rho_v) - (\tau_v + \rho_v) = \tau_u - \tau_v \quad (2)$$

Two different measurements should yield the same $\underline{\epsilon}$, i.e. the first and the second complex permittivity of the object (left and right equation side in Eq. (3)):

$$\frac{\oiint_{\partial A_{xyz}} \nabla \underline{H}_u^+ dr}{\int_{A_{xyz}} \underline{H}_u^+ dV} = \underline{\epsilon}_u = \underline{\epsilon}_v = \frac{\oiint_{\partial A_{xyz}} \nabla \underline{H}_v^+ dr}{\int_{A_{xyz}} \underline{H}_v^+ dV}. \quad (3)$$

In this equation, replacing the phase distribution $\tau_v$ by $\tau_v = \tau_u - \delta_{uv}$, the first complex permittivity (left hand side in Eq. (4)) comprises the first amplitude of the given magnetic field component and the second complex permittivity ((right hand side in Eq. (4)) comprises the second amplitude of the given magnetic field component and the phase difference:

$$\frac{\oiint_{\partial A_{xyz}} \nabla \{H_u^+ \exp(i\tau_u)\} dr}{\int_{A_{xyz}} \{H_u^+ \exp(i\tau_u)\} dV} = \frac{\oiint_{\partial A_{xyz}} \nabla \{H_v^+ \exp(i\tau_u - i\delta_{uv})\} dr}{\int_{A_{xyz}} \{H_v^+ \exp(i\tau_u - i\delta_{uv})\} dV}, \quad (4)$$

Eq. (4) contains only the single unknown $\tau_u$, since the field amplitudes and $\delta_{uv}$ can be measured exactly. The differential structure of Eq. (4) makes it easier to numerically iterate the correct $\tau^u$ (i.e. the phase of the given magnetic field component for the first coil position) than to extract it analytically. An example how to numerically iterate $\tau_u$ is given below. Once $\tau_u$ is determined, $\tau_v$, $\rho_u$, $\rho_v$ etc. can be calculated straight-forward via Eqs. (1, 2). Two transmit channels are sufficient for this procedure. Of course, the redundancy obtained using more than two transmit channels can be used to stabilize the reconstruction.

For the calculation of local SAR via $$SAR(\vec{r}) = \frac{1}{2}\sigma(\vec{r})\vec{E}(\vec{r})\vec{E}^*(\vec{r}) \quad (5)$$

$$= \frac{\sigma(\vec{r})}{2\omega^2\varepsilon^2(\vec{r})}(\vec{\nabla}\times\vec{H}(\vec{r}))(\vec{\nabla}\times\vec{H}^*(\vec{r})),$$

all three spatial magnetic field components are required. In the following, a method is sketched how to obtain all required components applying further iterations of the kind described above.

For a certain Tx channel u, the amplitude of $H_u^+$ is measured traditionally.

The phase of $H_u^+$, i.e. $\tau_u$, is determined iteratively via Eq. (4) as described above.

The phase of $H_u^+$, i.e. $\rho_u$, is determined via $\phi_{uu}$ (cf. Eq. (1)).

The amplitude of $H_u^-$, is determined via an iteration according to Eq. (4)

$$\frac{\oint\!\!\!\oint_{\partial A_{xyz}}\nabla\{H_u^+\exp(i\tau_u)\}d\vec{r}}{\int_{A_{xyz}}\{H_u^+\exp(i\tau_u)\}dV} = \frac{\oint\!\!\!\oint_{\partial A_{xyz}}\nabla\{H_u^-\exp(i\rho_u)\}d\vec{r}}{\int_{A_{xyz}}\{H_u^-\exp(i\rho_u)\}dV}, \quad (6)$$

i.e. conductivity reconstructions based on $H^+$ or $H^-$ should yield identical results.

After determination of $H^+$ and $H^-$, the corresponding Cartesian components can be calculated via the definition of the circularly polarized components $H^+$ and $H^-$ $$H^+=(H_x+iH_y)/2;\ H^-=(H_x-iH_y)/2. \quad (7)$$

The final missing component Hz can be determined via (magnetic) Gauss' law $$\partial_z H_z = \partial_x H_x - \partial_y H_y. \quad (8)$$

An iteration similar to that for Eq. (4) can be performed for Eq. (6). Alternatively, Eqs. (7, 8) can be combined, i.e., Gauss' law can be written for the circular field components, making the explicit calculation of the Cartesian components redundant. The real and the imaginary part of Eq. (8) can be iterated separately, yielding amplitude and phase of $H_z$.

Now, amplitude and phase of all three spatial magnetic field components are determined, enabling the highly accurate determination of local SAR via Eq. (5).

In accordance with a further embodiment of the invention, the method further comprises a spatial segmentation of the object, wherein the segmentation is performed such that in each segment the ratio of the variation of the complex permittivity and the electric field component of the excitation RF field is below a predetermined threshold, wherein the method if performed individually for each segment. For example, the segmentation is performed by spatially analyzing a variation of nuclear spin relaxation, for example a variation in $T_1$ and/or $T_2$ in said object.

This has also the advantage, that a performance of electric properties tomography imaging of an object can be performed at higher accuracy since the general inaccurate assumption in state of the art reconstruction processes that for the whole object to be examined the total variation of the complex permittivity is much smaller than the variation of the electric field does not have to be used anymore. Consequently, the results in electric properties tomography imaging are adapted much more to reality and do not rely anymore on such kind of inaccurate general assumptions.

In detail, the state of the art model assumption is $\delta\sigma$, $\delta\epsilon\ll\delta E$, i.e. in the vicinity of the reconstructed voxel, the variation of conductivity and permittivity has to be much smaller than the variation of the electric field (published for example in IEEE Transactions on Medical Imaging, Vol. 28, No. 9, pp. 1365ff, September 2009). To circumvent this assumption, reconstruction is performed on segmented compartments with constant conductivity and permittivity. Preferably, numerically flexible calculus operations may be applied to enable reconstruction also along the boundary of the segmented compartments.

The segmentation may be performed, e.g., on the anatomic MR images acquired for the B1 or B0 mapping performed for EPT. Alternatively, the segmentation can be performed on the T1 map, which might be acquired simultaneously with the B1 map (see, e.g., Tobias Voigt, Ulrich Katscher, Kay Nehrke, Olaf Doessel, Simultaneous B1 and T1 Mapping Based on Modified "Actual Flip-Angle Imaging", ISMRM 17 (2009) 4543). Of course, also a suitable combination of all of these images might be used for segmentation. In the resulting, segmented compartments with same T1 and T2, it is assumed that $\underline{\epsilon}$ is constant, and thus, $\delta\underline{\epsilon}\ll\delta E$ is fulfilled.

Numerically flexible calculus operations may be applied inside the segmented compartments, i.e., the number of side voxels entering the various numerical calculus operations is adapted to the (maybe limited) number of voxels available inside the (maybe small) compartment. Particularly, the number of entering side voxels can differ from side to side according to the individual neighborhood of the current voxel (i.e., using numerically "asymmetric" calculus operations). This enables EPT reconstruction also along the boundaries of the segmented compartments.

Besides ensuring $\delta\underline{\epsilon}\ll\delta\underline{E}$, the restriction of the discussed calculus operations to segmented compartments implies a second advantage. Discontinuities of $\underline{\epsilon}$ can lead to discontinuities in the first derivative of the magnetic field. Such discontinuities can corrupt numerical differentiation. Please note that this is not a question of model assumptions but a question of numerical implementation of differential operations.

Both symmetric and asymmetric calculus operations might require at least one pixel on each side of the current voxel. In these cases, $\underline{\epsilon}$ may not be calculated for the boundary voxel itself, leading to a gap of at least two undefined voxels between two combined compartments. However, this gap can be closed by extrapolating the boundary voxels from the inner, non-boundary voxels of the compartment.

Reconstruction can be stabilized by assigning a single, constant value $\underline{\epsilon}$ to each segmented compartment. This constant $\underline{\epsilon}$ can be calculated, e.g., as average over the spatial distribution of the pixel-by-pixel reconstruction of $\underline{\epsilon}$ inside the regarded compartment. The compartment's average of $\underline{\epsilon}$ can be coded as brightness of the pixel; simultaneously, the compartment's standard deviation of $\underline{\epsilon}$ can be color coded.

In accordance with a further embodiment of the invention, the method further comprises determining an anisotropy of a given complex permittivity, for example the first or second complex permittivity. The anisotropy determination comprises selecting a first and a second spatial reconstruction plane of the object and reconstructing the given complex permittivity along said first reconstruction plane and said second reconstruction plane, said reconstruction resulting in a new first complex permittivity for the first reconstruction plane and a new second complex permittivity for the second reconstruction plane. The anisotropy of the given complex permittivity is then determined from the variation between said new first complex permittivity and said new second complex permittivity.

In detail, $\underline{\epsilon}$ can be reconstructed by (IEEE Transactions on Medical Imaging, Vol. 28, No. 9, pp. 1365ff, September 2009):

$$\frac{\oint_{\partial A} \vec{\nabla} \times \vec{H}(\vec{r}) d\vec{r}}{\mu_0 \omega^2 \int_A \vec{H}(\vec{r}) d\vec{a}} = \frac{\oint_{\partial A} \underline{\varepsilon}'(\vec{r}) \vec{E}(\vec{r}) d\vec{r}}{\oint_{\partial A} \vec{E}(\vec{r}) d\vec{r}} \qquad (9)$$

$$= \frac{\oint_{\partial A} \{(\varepsilon_{xx} E_x + \varepsilon_{xy} E_y + \varepsilon_{xz} E_z), (\varepsilon_{yx} E_x + \varepsilon_{yy} E_y + \varepsilon_{yz} E_z), (\varepsilon_{zx} E_x + \varepsilon_{zy} E_y + \varepsilon_{zz} E_z)\} d\vec{r}}{\oint_{\partial A} \{(E_x + E_y + E_z), (E_x + E_y + E_z), (E_x + E_y + E_z)\} d\vec{r}},$$

where $\underline{\varepsilon}'$ now indicates the general tensor form of the above used scalar $\underline{\varepsilon}$. For example, for coronal (xz) and sagittal (yz) reconstruction planes, Eq. (9) reduces to Eqs. (10, 11), respectively $$\frac{\oint_{\partial A} \underline{\varepsilon}'(\vec{r}) \vec{E}(\vec{r}) d\vec{r}}{\oint_{\partial A} \vec{E}(\vec{r}) d\vec{r}} = \frac{\oint_{\partial A_{xz}} \{(\varepsilon_{xx} E_x + \varepsilon_{xy} E_y + \varepsilon_{xz} E_z), (\varepsilon_{zx} E_x + \varepsilon_{zy} E_y + \varepsilon_{zz} E_z)\} d\vec{r}}{\oint_{\partial A_{xz}} \{(E_x + E_y + E_z), (E_x + E_y + E_z)\} d\vec{r}}, \qquad (10)$$

$$\frac{\oint_{\partial A} \underline{\varepsilon}'(\vec{r}) \vec{E}(\vec{r}) d\vec{r}}{\oint_{\partial A} \vec{E}(\vec{r}) d\vec{r}} = \frac{\oint_{\partial A_{yz}} \{(\varepsilon_{yx} E_x + \varepsilon_{yy} E_y + \varepsilon_{yz} E_z), (\varepsilon_{zx} E_x + \varepsilon_{zy} E_y + \varepsilon_{zz} E_z)\} d\vec{r}}{\oint_{\partial A_{yz}} \{(E_x + E_y + E_z), (E_x + E_y + E_z)\} d\vec{r}}. \qquad (11)$$

However, it has to be noted that any suitable reconstruction planes adapted to the patient anatomy (or the spatial object structure in general) may be used.

The isotropic case described above is given by $\underline{\varepsilon}_{ij} = \underline{\varepsilon}_{iso}$ for all i,j=x,y,z, and Eqs. (10, 11) (i.e. the new first and second complex permittivities) read $$\frac{\oint_{\partial A} \underline{\hat{\varepsilon}}'(\vec{r}) \vec{E}(\vec{r}) d\vec{r}}{\oint_{\partial A} \vec{E}(\vec{r}) d\vec{r}} = \frac{\oint_{\partial A_{xz}} \varepsilon_{iso} \{(E_x + E_y + E_z), (E_x + E_y + E_z)\} d\vec{r}}{\oint_{\partial A_{xz}} \{(E_x + E_y + E_z), (E_x + E_y + E_z)\} d\vec{r}} \qquad (12)$$

$$\approx \frac{\varepsilon_{iso}(\vec{r}) \oint_{\partial A} \vec{E}(\vec{r}) d\vec{r}}{\oint_{\partial A} \vec{E}(\vec{r}) d\vec{r}}$$

$$= \varepsilon_{iso}(\vec{r}),$$

$$\frac{\oint_{\partial A} \underline{\varepsilon}'(\vec{r}) \vec{E}(\vec{r}) d\vec{r}}{\oint_{\partial A} \vec{E}(\vec{r}) d\vec{r}} = \frac{\oint_{\partial A_{yz}} \varepsilon_{iso} \{(E_x + E_y + E_z), (E_x + E_y + E_z)\} d\vec{r}}{\oint_{\partial A_{yz}} \{(E_x + E_y + E_z), (E_x + E_y + E_z)\} d\vec{r}} \qquad (13)$$

$$\approx \frac{\varepsilon_{iso}(\vec{r}) \oint_{\partial A} \vec{E}(\vec{r}) d\vec{r}}{\oint_{\partial A} \vec{E}(\vec{r}) d\vec{r}}$$

$$= \varepsilon_{iso}(\vec{r}).$$

Now, an example of maximum anisotropy assuming $\underline{\varepsilon}$ parallel to the coronal plane (xz) is investigated, i.e., $\underline{\varepsilon}_{ij}=0$ for all i,j=x,y,z besides $\underline{\varepsilon}_{xx}$. Thus, Eqs. (12, 13) can be re-written and read in this case as the new first and second complex permittivities as $$\frac{\oint_{\partial A} \underline{\varepsilon}'(\vec{r}) \vec{E}(\vec{r}) d\vec{r}}{\oint_{\partial A} \vec{E}(\vec{r}) d\vec{r}} = \frac{\oint_{\partial A_{xz}} \{(\varepsilon_{xx} E_x, 0)\} d\vec{r}}{\oint_{\partial A_{xz}} \{(E_x + E_y + E_z), (E_x + E_y + E_z)\} d\vec{r}} \qquad (14)$$

$$\approx \frac{\varepsilon_{xx} \oint_{\partial A_{xz}} \{E_x, 0\} d\vec{r}}{\oint_{\partial A_{xz}} \{(E_x + E_y + E_z), (E_x + E_y + E_z)\} d\vec{r}}$$

$$= \varepsilon_{xx} f(\vec{E}),$$

$$\frac{\oint_{\partial A} \underline{\varepsilon}'(\vec{r}) \vec{E}(\vec{r}) d\vec{r}}{\oint_{\partial A} \vec{E}(\vec{r}) d\vec{r}} = \frac{\oint_{\partial A_{yz}} \{0, 0\} d\vec{r}}{\oint_{\partial A_{yz}} \{(E_x + E_y + E_z), (E_x + E_y + E_z)\} d\vec{r}} \qquad (15)$$

$$= 0.$$

Thus, the reconstruction yields a minimum for a plane orientation perpendicular to the anisotropic $\underline{\varepsilon}$.

In accordance with a further embodiment of the invention, the given magnetic field component is a positive circularly polarized magnetic field component of the excitation RF field at a first coil position, wherein the method further comprises determining a negative circularly polarized magnetic field component at a first coil position, wherein said determination of the negative circularly polarized magnetic field component comprises determining a first geometrical symmetry plane of the object, wherein the second coil position is given by a reflection of the first coil position against said first symmetry plane.

Further, a first map of the positive circularly polarized magnetic field component of the excitation RF field at a second coil position is determined and a second map of the negative circularly polarized magnetic field component at a first coil position is determined by a reflection of the first map against the second geometrical symmetry plane in the first map. Here, the position of the second symmetry plane in the second map is equivalent to the position of the first symmetry plane in the object, i.e. the virtual position of the symmetry plane in the object has to be virtually transferred to a respective location in the second map. Finally, the negative circularly polarized magnetic field component at the first coil position is determined from the second map.

By applying multiple measurements with parallel RF transmission, spatial patient symmetries can be utilized to estimate the magnetic field component $H^-$, particularly required for estimating local SAR. By carrying out the method steps as discussed above, an estimation for $H^-$ is obtained which yields better SAR estimations than assuming simply $H^-=0$.

In another aspect, the invention relates to a magnetic resonance method of electric properties tomography imaging of an object, the method comprising applying an excitation RF field to the object via a coil at a first spatial coil position and via a coil at a second spatial coil position. Again, the application of the excitation RF field is performed subsequently in time via the first and second spatial coil position. Then, a first geometrical symmetry plane of the object is determined, wherein the second coil position is given by a reflection of the first coil position against said first symmetry plane. A first map of a positive circularly polarized magnetic field component of the excitation RF field at a second coil position is determined, followed by the determination of a second map of a negative circularly polarized magnetic field component at a first coil position by a reflection of the first map against a second geometrical symmetry plane in the first map, wherein the position of the second symmetry plane in the second map is equivalent to the position of the first symmetry plane in the object. Finally, a negative circularly polarized magnetic field component at a first coil position is determined from the second map.

In another aspect, the invention relates to a magnetic resonance method of electric properties tomography imaging of an object, the method comprising applying an excitation RF field to the object via a coil and acquiring resulting magnetic resonance signals via a receiving channel from the object. Then, from the acquired magnetic resonance signals a magnetic field component of the excitation RF field of the coil is determined and a complex permittivity is calculated by dividing a surface volume integral of the gradient of said determined magnetic field component by a volume integral of said determined magnetic field component.

By means of this improved EPT reconstruction technique, the number of required spatial magnetic field components can be reduced. Specifically, conductivity and permittivity can be reconstructed on the basis of a single field component, the (easy to measure) RF transmission field.

In detail, as also mentioned above, in the framework of EPT, the electric conductivity $\sigma$ and permittivity $\epsilon$ (combined to $\epsilon-i\sigma/\omega=\underline{\epsilon}$) are linked to the magnetic field components via $$\underline{\epsilon}(\vec{r})\mu_0\omega^2\int_A \vec{H}(\vec{r})d\vec{a} = \oint_{\partial A} \vec{\nabla} \times \vec{H}(\vec{r})d\vec{r} \tag{16}$$

with A denoting the integration area and $\partial A$ the curve around this area. The electric properties $\underline{\epsilon}$ are assumed to be constant inside area A or nearly constant as discussed above. Eq. (16) contains all three components of the magnetic field. In the following, the EPT equation (16) may be written as a function of $H^+$ only, as already used for Eqs (4,6).

As a first step, we change the coordinate system. The magnetic field vector can be expressed as $$H'^T=(H^+,H^-,H_z)^T \tag{17}$$

In the following, primes will be omitted since all expressions are given in the new coordinates (unless explicitly stated).

The second step is, to recast Eq. (16) that it solely depends on one component of the magnetic field vector. The placement of the area A in space will be used to achieve this goal. Setting A equal to the yz plane ($A=A_{yz}$), perpendicular to the x-axis, yields $$\underline{\epsilon}(\vec{r})\mu_0\omega^2\int_{A_{yz}} \underline{H}_x(\vec{r})d\vec{a} = \oint_{\partial A_{yz}} \vec{\nabla} \times \vec{H}(\vec{r})d\vec{r}. \tag{18}$$

$H_x$ denotes the x-component of the magnetic field vector. Both sides are now integrated along the x direction $$\underline{\epsilon}(\vec{r})\mu_0\omega^2\int_V \underline{H}_x(\vec{r})dV = \int_{A_x}\left\{\oint_{\partial A_{yz}} \vec{\nabla} \times \vec{H}(\vec{r})d\vec{r}\right\}dx. \tag{19}$$

Application of Stokes theorem on the right side of Eq. (19) leads to $$\underline{\epsilon}\mu_0\omega^2\int_V \underline{H}_x dV = \int_{C_x}\{\int_{A_{yz}} \nabla \times \nabla \times \vec{\underline{H}} d\vec{a}\}dx. \tag{20}$$

It is $d\vec{a}|e_x x d a\| e_x x$ and $(\nabla \times \nabla \times \underline{\vec{H}})_x = -\nabla \cdot \nabla \underline{H}_y (\nabla \times \nabla \times \underline{H})_x = -\nabla \cdot \nabla \underline{H}_y$, which, using Gauss theorem, can be written as $$\underline{\epsilon}\mu_0\omega^2\int_V \underline{H}_x dV = -\int_V \nabla \cdot \nabla \underline{H}_x dV = -\oiint_{\partial V} \nabla \underline{H}_x \cdot d\vec{a}. \tag{21}$$

Using Eq. (17), Eq. (21) can now be written for the measurable field component $$\underline{\epsilon}\mu_0\omega^2\int_V \underline{H}_+ dV = -\oiint_{\partial V} \nabla \underline{H}_+ \cdot d\vec{a}, \tag{22}$$

i.e., the wanted spatial distribution of $\underline{\epsilon}$ is given by $$\underline{\epsilon}=-\oiint_{\partial V} \nabla \underline{H}_+ \cdot d\vec{a} / (\mu_0\omega^2\int_V \underline{H}_+ dV). \tag{23}$$

This equation does not require the explicit calculation of the second spatial derivative, which is of crucial importance for numerical stability.

By means of Eq. (23), electric properties can be reconstructed exactly with the knowledge of $\underline{H}^+$ only. The magnitude of $\underline{H}^+$ can be determined via standard B1 mapping. A phase estimation can further be performed as described above in detail.

One disadvantage of standard B1 mapping for determining the magnitude of $\underline{H}^+$ is that such respective measurements typically require two or more scans with different flip angles and/or different repetition times (compare Yarnykh V L. Actual flip-angle imaging in the pulsed steady state: a method for rapid three-dimensional mapping of the transmitted radiofrequency field. MRM 57 (2007) 192-200 and Tobias Voigt, Ulrich Katscher, Kay Nehrke, Olaf Doessel, Simultaneous B1 and T1 Mapping Based on Modified "Actual Flip-Angle Imaging", ISMRM 17 (2009) 4543).

The numerical differentiation of the EPT reconstruction is rather noise sensitive and thus B1 maps must be acquired with high SNR, which additionally increases scan time particularly for the usual high spatial resolution.

These problems are all overcome by an embodiment of the invention, in which the magnetic field component comprises an amplitude component and a phase component, wherein the method comprises determining only the phase component of the magnetic field component, the method further comprising splitting said complex permittivity into a real part describing a permittivity component and an imaginary part describing a conductivity component and neglecting in the imaginary part the amplitude component of the magnetic field component for calculating from the phase component of the magnetic field component the conductivity component.

Consequently, a conductivity reconstruction is performed based only on the B1 phase. This shortens the required measurements considerably since for example a simple 3D (turbo-) spin echo sequence is sufficient as B1 phase scan.

In accordance with a further embodiment of the invention, the method further comprises neglecting in the real part the phase component of the magnetic field component for calculating from the amplitude component of the magnetic field component the permittivity component. Consequently, also a permittivity reconstruction method is presented which is based only on the B1 amplitude.

In accordance with a further embodiment of the invention, the neglect of the amplitude component is performed by setting the amplitude component to a constant value.

The complex B1 map $\underline{H}^+ = H^+ \exp(i\varphi^+)$ in the numerator of Eq. (23) can be differentiated via the product rule $$\frac{-\oiint_{\partial A_{xyz}} \nabla\{H^+ \exp(i\varphi^+)\} da}{\mu_0 \omega^2 \int_{A_{xyz}} H^+ \exp(i\varphi^+) dV} = \tag{25}$$

$$-\frac{\oiint_{\partial A_{xyz}} \exp(i\varphi^+) \nabla H^+ da}{\mu_0 \omega^2 \int_{A_{xyz}} \exp(i\varphi^+) H^+ dV} - i \frac{\oiint_{\partial A_{xyz}} H^+ \exp(i\varphi^+) \nabla \varphi da}{\mu_0 \omega^2 \int_{A_{xyz}} H^+ \exp(i\varphi^+) dV}.$$

with $\omega$ denoting the Larmor frequency and $\mu_0$ the vacuum permeability. Here, $\varphi^+$ generally denotes the phase component of the positive circularly polarized magnetic field component $\underline{H}^+$ and $H^+$ denotes the amplitude component of the positive circularly polarized magnetic field component $\underline{H}^+$.

Real and imaginary part of the r.h.s of Eq. (25) can be associated with the definition of complex permittivity $\underline{\epsilon} = \epsilon - i\sigma/\omega$, and identical terms in numerator and denominator, $\exp(i\varphi^+)$ and $H^+\exp(i\varphi^+)$, approximately cancel out:

$$-\frac{\oiint_{\partial A_{xyz}} \exp(i\varphi^+) \nabla H^+ da}{\mu_0 \omega^2 \int_{A_{xyz}} \exp(i\varphi^+) H^+ dV} \approx -\frac{\oiint_{\partial A_{xyz}} \nabla H^+ da}{\mu_0 \omega^2 \int_{A_{xyz}} H^+ dV} \approx \epsilon, \tag{26a}$$

$$\frac{\oiint_{\partial A_{xyz}} H^+ \exp(i\varphi^+) \nabla \varphi^+ da}{\mu_0 \omega^2 \int_{A_{xyz}} H^+ \exp(i\varphi^+) dV} \approx -\frac{\oiint_{\partial A_{xyz}} \nabla \varphi^+ da}{\mu_0 \omega A_{xyz}} \approx \sigma. \tag{26b}$$

Thus, $\epsilon$ is predominantly determined by the amplitude $H^+$, and $\sigma$ is predominantly determined by the phase $\varphi^+$. According to the simulations described below, approximation (26)a particularly works for $\omega\epsilon \gg \sigma$, and approximation (26)b particularly works for $\omega\epsilon \ll \sigma$.

The corresponding accurate calculation of $\sigma$ and $\epsilon$ yields $$\Re\left[\frac{-\oiint_{\partial A_{xyz}} \nabla \underline{H}^+ da}{\mu_0 \omega^2 \int_{A_{xyz}} \underline{H}^+ dV}\right] = \left(\mu_0 \omega^2 \int_{A_{xyz}} H^+ dV\right)^{-1} \tag{27a}$$

$$\left(-\oiint_{\partial A_{xyz}} \nabla H^+ da + \int_{A_{xyz}} H^+ (\nabla \varphi^+)^2 dV\right)$$

$$= \epsilon,$$

$$\Im\left[\frac{-\oiint_{\partial A_{xyz}} \nabla \underline{H}^+ da}{\mu_0 \omega^2 \int_{A_{xyz}} \underline{H}^+ dV}\right] = (\mu_0 \omega A_{xyz})^{-1} \tag{27b}$$

$$\left(\oiint_{\partial A_{xyz}} \nabla \varphi^+ da + \int_{A_{xyz}} 2\frac{\nabla H^+}{H^+} \cdot \nabla \varphi^+ dV\right)$$

$$= \sigma.$$

It is not intuitive that the additional terms in Eqs. (27)a,b are negligible to end up with Eqs. (26)a,b. However, it shows that the approximate reconstruction via Eqs. (26)a,b is equivalent with the full reconstruction via Eq. (24) assuming $H^+$=const in Eq. (27)b or $\varphi^+$=const in Eq. (27)a, respectively. Thus, a separate, numerical implementation of Eq. (26) is not mandatory, however, roughly cut in half calculation time.

The method of the invention can be advantageously carried out in most MR devices in clinical use at present. Therefore, the invention also relates to a magnetic resonance system for performing electric properties tomography imaging of an object, the system being arranged to carry out the method steps described above. To this end, it is merely necessary to utilize a computer program by which the MR device is controlled such that it performs the above explained method steps of the invention. The computer program may be present either on a data carrier or be present in a data network so as to be downloaded for installation in the control unit of the MR device. Therefore, the invention also relates to a computer program product comprising computer executable instructions to perform the method as described above.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF EMBODIMENTS

Figure 1:
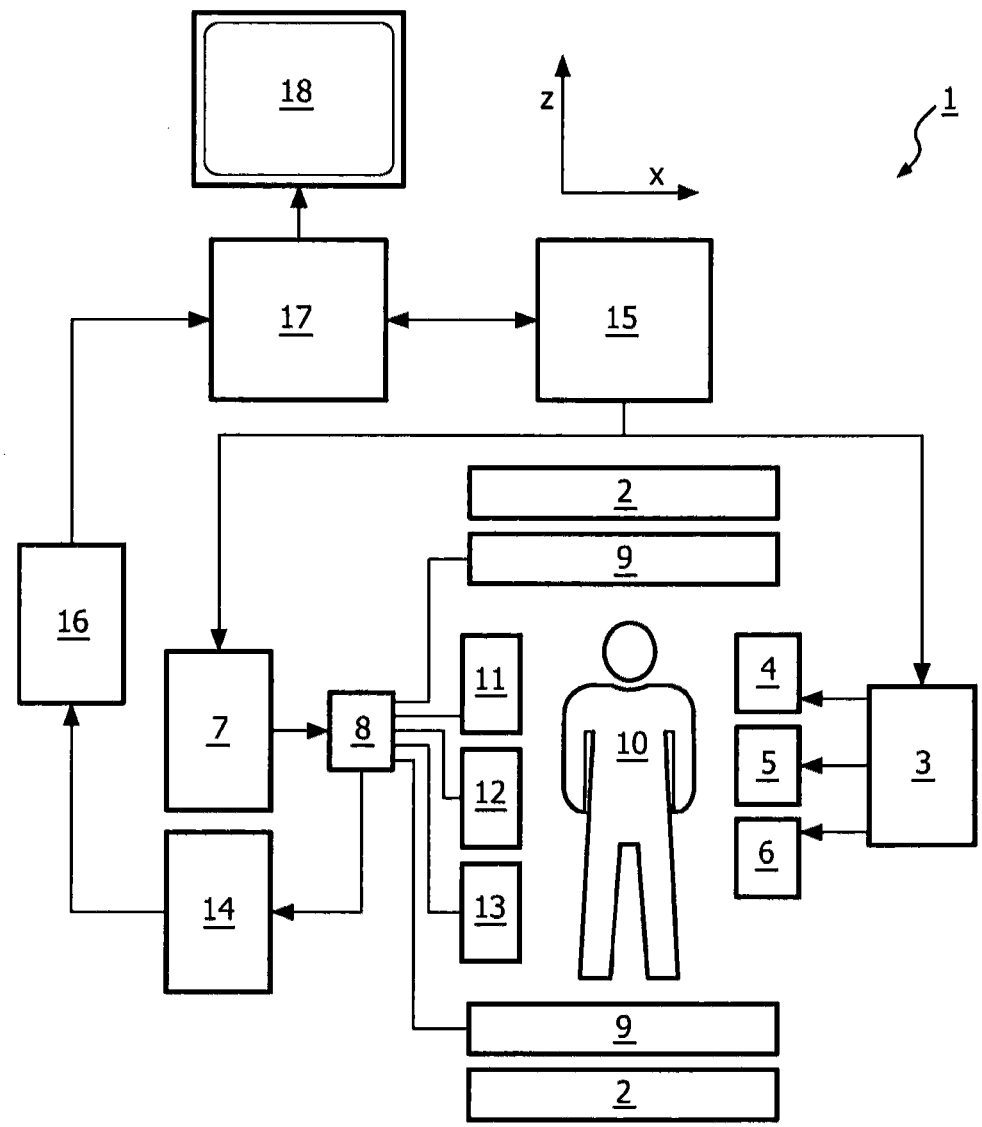
FIG. 1 shows an MR device for carrying out the method of the invention.

FIG. 1 shows diagrammatically an electric impedance imaging system in the form of a magnetic resonance imaging system that is adapted for performing electric properties tomography imaging of an object.

A magnetic resonance generation and manipulation system 1 applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A RF transmitter 7 transmits RF pulses or pulse packets, via a send-/receive switch 8, to a RF antenna 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body 10, for example by means of parallel imaging, a set of local array RF coils 11, 12, 13 are placed contiguous to the region selected for imaging. The array coils 11, 12, 13 can be used to receive MR signals induced by RF transmissions effected via RF antenna 9. However, as described above, the array coils 11, 12, 13 may also be used to sequentially transmit RF pulses into the examination volume.

The resultant MR signals are picked up by the RF antenna 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

For practical implementation of the invention, the MR device 1 comprises the programming for carrying out the above described method. The program may be carried out for example by the reconstruction means 17 or a further computer or hardware component attached to the device 1.

Figure 2:
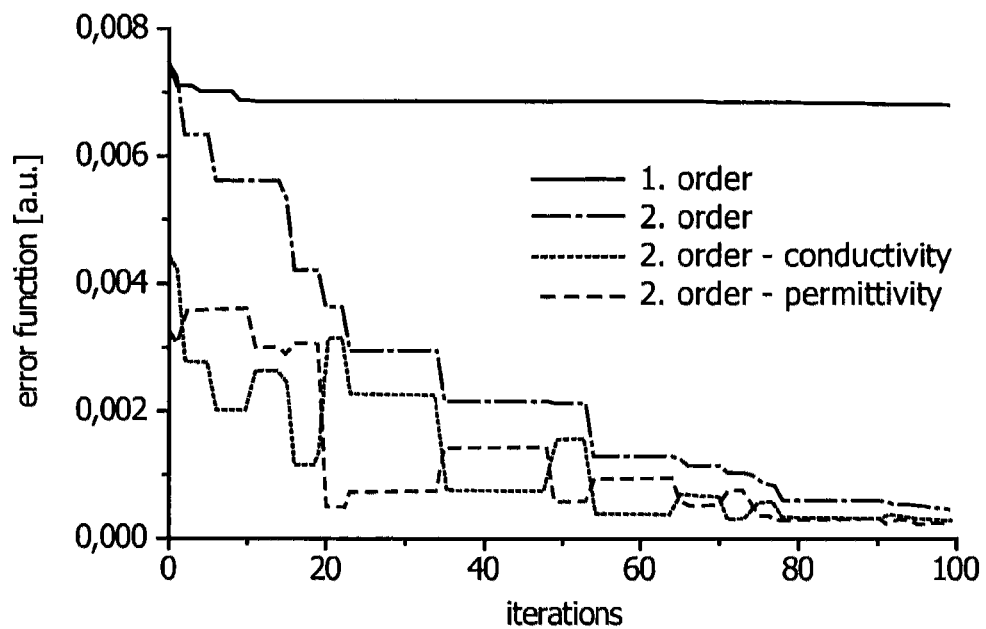
FIG. 2 illustrates an error function for first 100 steps iterating an unknown phase of a positive circularly polarized magnetic field component of an elliptical phantom with constant complex permittivity.

With respect to FIG. 2, an example implementation of the described iteration to determine $\tau_u$ is sketched.

A suitable function set $f_k$ has to be chosen to decompose the unknown phase distribution $\tau_u = \Sigma_k a_{ku} f_k$ using the superposition coefficients $a_{ku}$. An appropriate function set, which reflects the typically smooth nature of $\sigma_u$, ensures a minimum number of coefficients $a_{ku}$ required to approximate $\tau_u$. The easiest function set is given by delta peaks. In this case, however, each voxel is iterated separately, yielding the maximum number of required $a_{ku}$. A polynomial or Fourier function set is more appropriate to describe $\tau_u$ during the iteration.

The iteration can start, e.g. with a constant or randomly determined phase or with $\delta_{uv}$. The determination of $\tau_u$ inside the volume of interest (VOI) can be split into separate iterations on subvolumes of the VOI. This typically accelerates the calculation. However, for decreasing subvolumes, the risk of multiple solutions of Eq. (4) increases, and a suitable compromise has to be found.

A suitable error function E has to be chosen for minimization, e.g.

$$E = (\sigma_u - \sigma_v)^2 + \lambda(\epsilon_u - \epsilon_v)^2, \quad (28)$$

with λ a freely adjustable regularization parameter.

A simulation has been performed assuming two transmit (Tx) channels. A subvolume of 10×10×5 voxels inside an elliptical, off-center phantom with constant ε has been chosen. The 3D phase distribution was decomposed into (a) four 0./1.-order polynomials, (b) ten 0./1./2.-order polynomials.

FIG. 2 shows the error function for 100 iterations. As can be seen, including not only 0./1.-order polynomials but also 2.-order polynomials improves results. Using up to second order polynomials, the two underlying (regularized) terms of the error function are shown. Using up to first order polynomials yields larger iteration errors than using up to second order polynomials. Using up to second order polynomials, the two underlying terms of the error function Eq. (28) are shown, regularized with λ=0.001.

Figure 3:
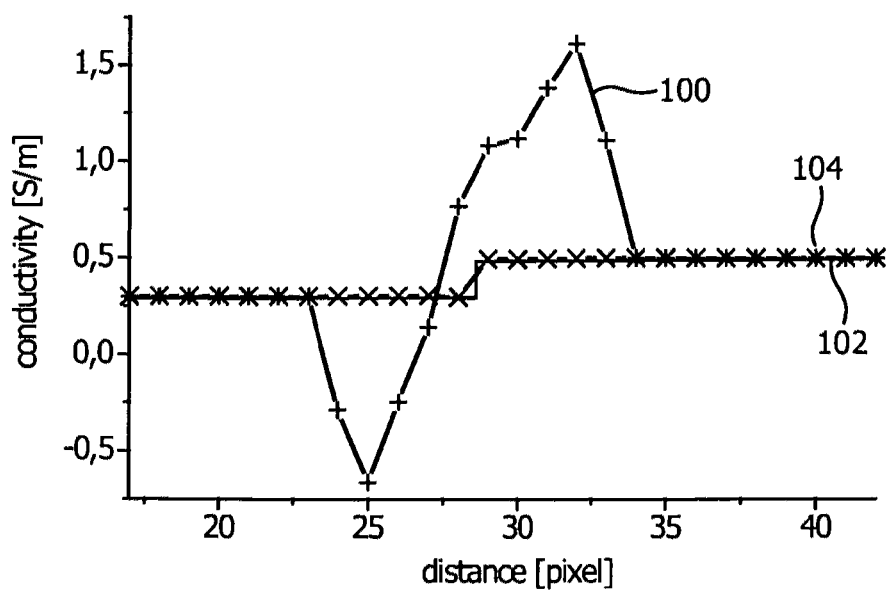
FIG. 3 illustrates simulated conductivity profiles of a spherical phantom.

FIG. 3 illustrates simulated conductivity profiles of a spherical phantom. EPT reconstruction was performed on segmented compartments. As mentioned above, the segmentation can be performed e.g. on the anatomic MR images acquired for the B1 or B0 mapping performed for EPT.

In FIG. 3, a comparison between EPT reconstruction with and without segmentation is given, using a simulated, spherical phantom with σ=0.3 (0.5) S/m in the left (right) hemisphere. A strong ringing artefact along the compartment boundary can be removed by the described segmentation technique in combination with the flexible calculus operations. Further, according to the above described method, boundary voxels were extrapolated from the next two non-boundary voxels of the corresponding compartment. A pixel-by-pixel reconstruction is plotted in FIG. 3.

As can be seen in FIG. 3, the conductivity 100 determined without segmentation deviates strongly from the true conductivity 102 at the area of transition from the left to the right hemisphere of the phantom. In contrast, by segmented EPT reconstruction a respective determined conductivity 104 reflects well the conductivity transition from the left phantom part to the right phantom part and vice versa.

FIG. 4 illustrates B1 maps simulated with FDTD for an eight channel transmit system. Exemplarily, local SAR was estimated via EPT and H$^+$ was simulated for the legs of a person in an eight channel transmit system. The simulation was performed using FDTD with the visible human at 5 mm grid resolution. The quadrature excitation (H$^+$>>H$^-$) was compared with a B1 shimmed excitation (H$^+$~H$^-$).

Figure 4A:
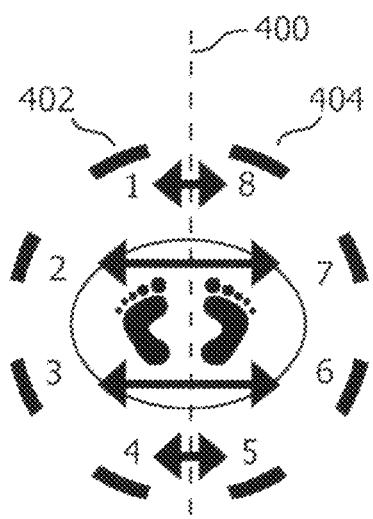
FIG. 4 (a, b) shows B1 maps simulated with FDTD (finite difference time domain method) for an eight channel transmit system.

FIG. 4a shows a transversal cut through the MR bore of the device. Shown are the feet of a person, wherein the feet have a geometrical symmetry plane 400. The position of coil number 1 (reference numeral 402) is given by a reflection of the spatial position of coil number 8 (reference numeral 404) against said symmetry plane 400. The same holds for the other illustrated coils 2, 3, 4, 5, 6 and 7.

Figure 4B:
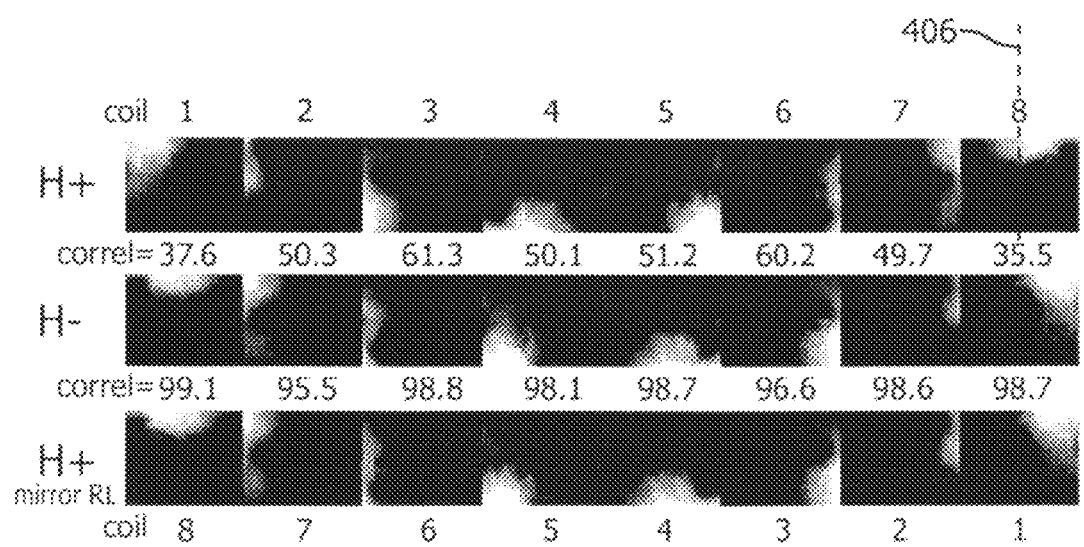

The top row in FIG. 4b shows a simulated map of the positive circularly polarized magnetic field component of the excitation RF field or each respective coil of the coils with numbers 1-8. Respective simulated maps of corresponding negative circularly polarized magnetic field components at the respective coil positions are illustrated in the second row of FIG. 4b. As expected, H$^+$ and H$^-$ have only a low correlation.

In a further step, second maps of the negative circularly polarized magnetic field components at the respective coil positions are reconstructed in the following manner: in order to reconstruct H$^-$ for coil number 1 which is located in FIG. 4a opposite to coil number 8, the map of the positive circularly polarized magnetic field component of the excitation RF field at coil position 8 is reflected against the geometrical symmetry plane 406. The position of this symmetry plane 406 is equivalent to the position of the symmetry plane 400 in the object. As a consequence, a right-left mirrored map of H$^+$ coil 8 is obtained, which correlates very well to H$^-$ at coil position 1, as shown in FIG. 4b. Consequently, due to the patient's approximate left-right symmetry, the mirrored H$^+$ maps have a correlation of 95 to 99% with the corresponding H$^-$ maps.

Figure 5A:
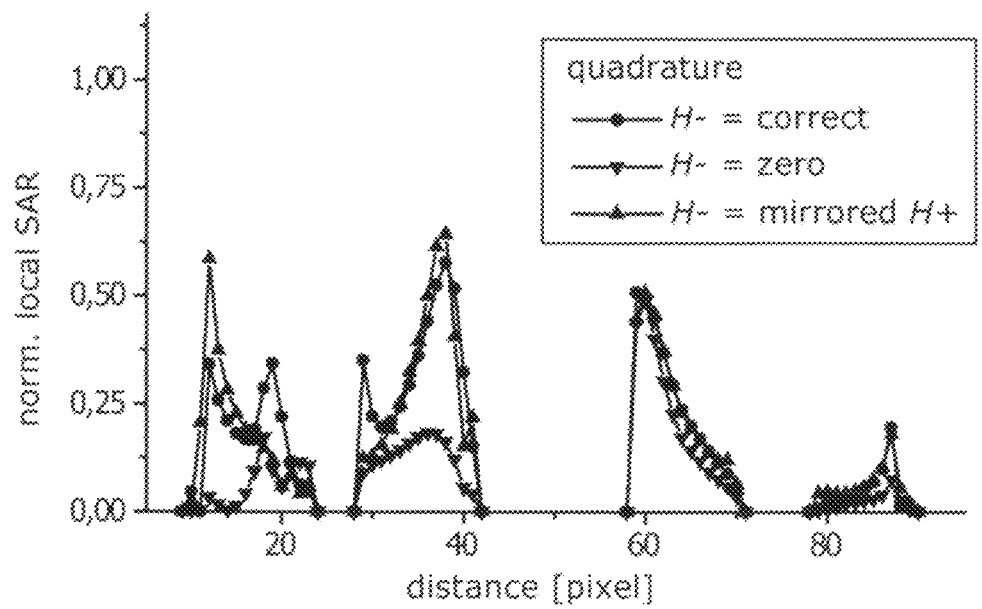
FIG. 5 (a, b) illustrates local SAR profiles of B1 maps in an eight channel system for two investigated cases (FDTD simulation)
Figure 5B:
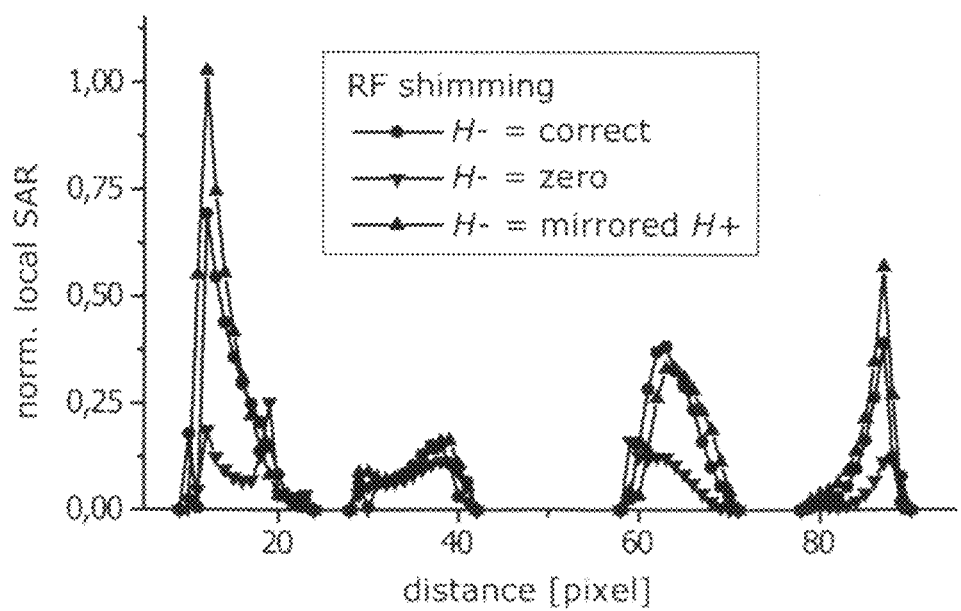

Employing this technique, local SAR profiles can be obtained in a highly reliable manner, as shown in FIG. 5. In FIG. 5a, a quadrature excitation was employed, whereas in FIG. 5b an RF shimming method was used. In both, the quadrature and the RF shimming case, H$^-$ has a high correlation with the correct local SAR as assuming H$^+$=0, particularly for the RF shimming case. Consequently, the simulation example shows that a proposed invention yields significantly better conductivity and local SAR reconstruction than neglecting H$^-$.

In the following, an alternative approach for determining the local SAR is discussed:

The local SAR given above in Eq. (5) can be rewritten to $$SAR_{loc} = \frac{\sigma}{2}\left(\frac{\nabla \times \vec{H}}{\iota\omega\varepsilon + \sigma}\right)^2.$$

In order to estimate the local SAR in accordance with the alternative approach outlined above with respect to Eq. (29), the following simplifications are performed:

By using a quadrature body or head coil, H$^-$=H$_z$=0 can be assumed. Further As described above, by measuring the phase $\phi^+$ employing for example by a (turbo-)spin echo sequence and setting the amplitude H$^+$ constant, σ can be obtained from Eq. (26)b. For example the amplitude H$^+$ is set constant to the nominal RF field strength of the scan proportional to B$_{1max}$ and flip angle, i.e. of the order of 10 μT. In opposite to the calculation of σ or ε, an absolute value is required for local SAR.

Further, for the estimation of the local SAR, ε is required. Here, three possibilities may be employed. First at all, since for most human tissue types ωε<<σ is fulfilled, ε=0 may be assumed. Alternatively, Eq. (27)a can be used to estimate ε via the measured $\phi^+$, i.e. by setting the amplitude H$^+$ constant. Alternatively, ε can be set to a constant value, e.g. to the ε of water.

Figure 6:
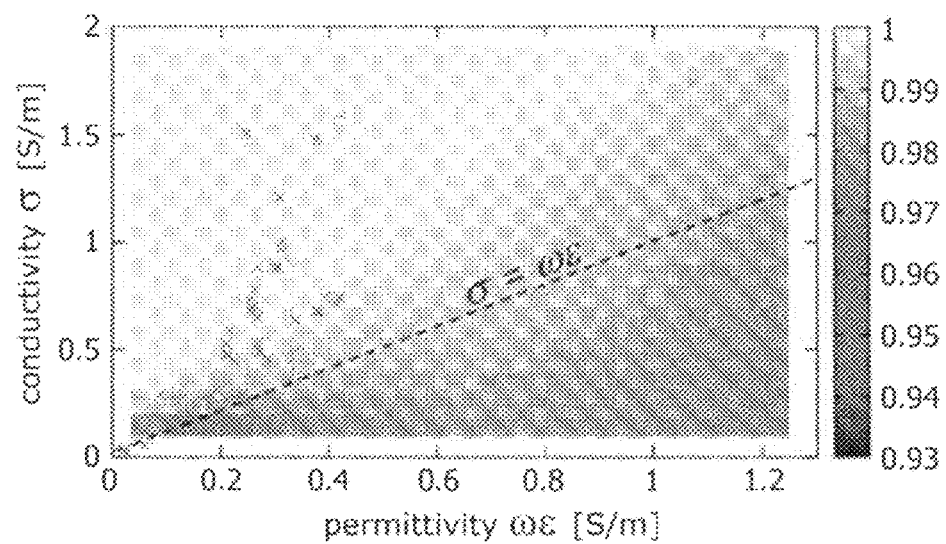
FIG. 6 illustrates the correlation of local SAR for standard EPT and EPT assuming H+=const.

In the following, the practical applicability of this approach for determining the local SAR is demonstrated:

First, the electromagnetic fields for a sphere with homogeneous electric properties in a quadratic body coil are simulated using the software package CONCEPT II (CONCEPT II, Technical University Hamburg-Harburg, Dep. Theo. Elec. Engin., Germany). Then, Eq. (29) is applied assuming H$^+$=const. This simulation was multiply repeated with 0.1 S/m<σ<1.9 S/m and 0.01 S/m<ωε<0.19 S/m. The correlation of local SAR between standard EPT and phase-based EPT was determined. As shown in FIG. 6, this correlation is found to be more than 95% for all reported types of human tissue (crosses) at a main magnetic field of 1.5 T.

Figure 7:
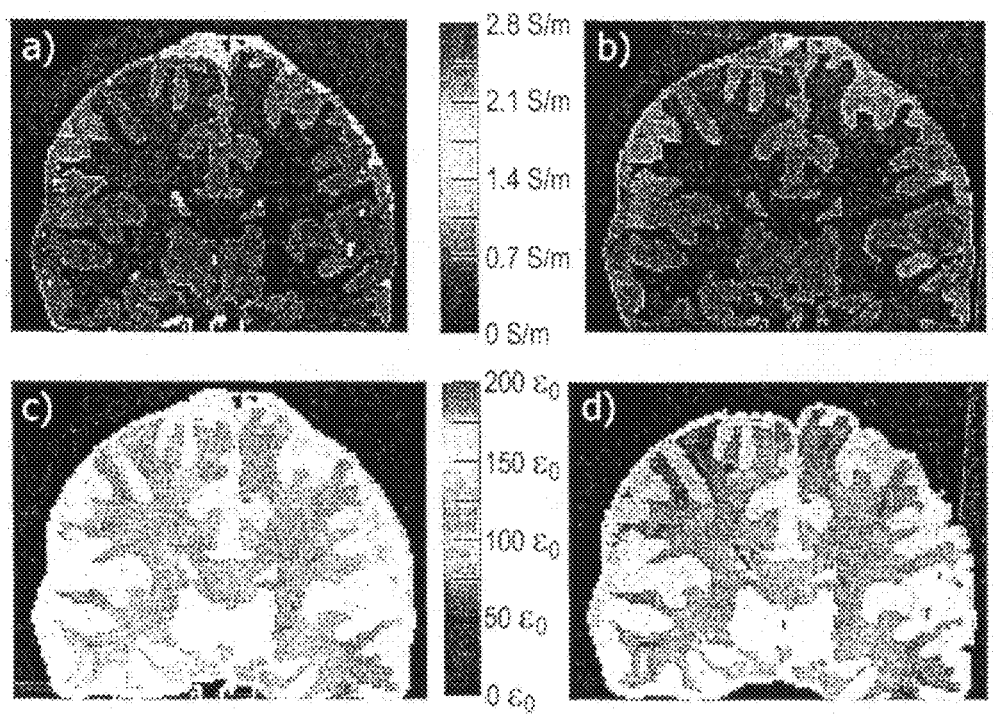
FIG. 7 (a, b, c, d) illustrate simulations comparing the reconstructed σ and the reconstructed ε of the head of the visible human.

In the following, the practical applicability of this approach for determining the permittivity and conductivity is demonstrated:

To this goal, the approach is applied to simulations based on the visible human (NLM 1996, "The visible human project"). Both the reconstructed σ assuming H$^+$=const as well as the reconstructed ε assuming $\phi^+$=const yields reasonable results. This can be seen from FIG. 7.

FIGS. 7a and 7b compare the reconstructed σ of the head of the visible human for the case of full reconstruction (FIG. 7a) and for the case of a reconstruction assuming H$^+$=const as discussed above (FIG. 7b). The correlation of the images is ~99%.

FIGS. 7c and 7d compare the reconstructed ε of the head of the visible human.

for the case of full reconstruction (FIG. 7c) and for the case of a reconstruction assuming $\phi^+$=const as discussed above (FIG. 7d). The main differences between the images are in pixels dominated by boundary errors, thus irrelevant.

Thus, the main impact of the assumption $\phi^+$=const on the reconstructed ε are found in pixels dominated by boundary errors, which is thus irrelevant and demonstrates well the practical applicability of this approach.

The invention claimed is:

1. A magnetic resonance method of electric properties tomography of an object, the method comprising:
   applying an imaging sequence that includes an excitation RF field to the object via a coil at a first spatial coil position, acquiring resulting magnetic resonance signals via a receiving channel from the object, determining from the acquired magnetic resonance signals a first phase distribution and a first amplitude of a first magnetic field component of the excitation RF field of the coil at the first spatial coil position,
   applying an excitation RF field to the object via a coil at a second spatial coil position, wherein the second spatial coil position is different from the first spatial coil position, acquiring resulting magnetic resonance signals via the receiving channel from the object, determining from the acquired magnetic resonance signals a second phase distribution and a second amplitude of a second magnetic field component of the excitation RF field of the coil at the second coil position, determining a phase difference distribution between the first and second phase distribution, determining a first and a second expression for the object's complex permittivity, the first expression for the complex permittivity expressed as a function of the first amplitude of the first magnetic field component and the second expression for the complex permittivity expressed as a function of the second amplitude of the second magnetic field component and the phase difference, equating the first complex permittivity and the second complex permittivity for receiving a final equation and determining from the final equation a phase of the given magnetic field component for the first coil position; and performing an electrical properties tomographic reconstruction using at least one of the first amplitude, the second amplitude, and the phase to generate an electrical properties tomographic image.

2. The method of claim 1, wherein in the final equation the phase of the given magnetic field component for the first coil position is approximated by a parametrizable function.

3. The method of claim 1, wherein the first magnetic field component is a positive circularly polarized magnetic field component of the excitation RF field at the first coil position, the method further including:

determining from the acquired magnetic resonance signals a negative circularly polarized magnetic field component at the first coil position.

4. The method of claim 1, wherein the electrical properties tomographic reconstruction determines an anisotropy of a the complex permittivity of the object on the basis of the first or the second complex permittivity expression.

5. The method of claim 1, wherein the first magnetic field component is a positive circularly polarized magnetic field component of the excitation RF field relative to the first coil position, the method further including:

determining a first geometrical symmetry plane of the object, such that the second coil position is a reflection of the first coil position relative to a symmetry plane, determining a first map of the positive circularly polarized first magnetic field component of the excitation RF field at the second coil position, determining a second map of a negative circularly polarized first magnetic field component at the first coil position by reflecting the first map relative to the symmetry plane.

6. A magnetic resonance method of electric properties tomography of an object, the method comprising:

applying an imaging sequence that includes an excitation RF field to the object via a coil at a first spatial coil position and acquiring first magnetic resonance signals, applying the imaging sequence via a coil at a second spatial coil position and acquiring second magnetic resonance signals, determining a geometrical symmetry plane of the object such that the second coil position is a reflection of the first coil position relative to said symmetry plane, with one or more processors, from the excitation RF field at the second coil position, determining a first map of a positive circularly polarized magnetic field component relative to the second coil position, with the one or more processors, determining a second map of a negative circularly polarized magnetic field component relative to the first coil position by reflecting the first map relative to the geometrical symmetry plane, with the one or more processors, determining a negative circularly polarized magnetic field component relative to the first coil position from the second map, with the one or more processors, from the first and second maps, generating a phase difference map, with the one or more processors, and from the phase difference map, generating a specific absorption rate (SAR) map or image, with the one or more processors.

7. A method of electric properties tomography imaging of an object, the method comprising:

applying imaging sequences that include excitation RF fields to the object via first and second coils and acquiring resulting first and second magnetic resonance signals via a receiving channel from the object, the first and second coils being at different locations, with one or more processors, determining from the first and second acquired magnetic resonance signals a magnetic field component of the excitation RF field of the coils, the magnetic field component including an amplitude component and a phase difference distribution, with the one or more processors, setting the amplitude component to a constant value, with the one or more processors, calculating a complex permittivity by dividing a surface volume integral of the gradient of said determined magnetic field phase difference distribution by a volume integral of said determined magnetic field phase difference distribution, with the one or more processors, splitting said complex permittivity into a real part describing a permittivity component and an imaginary part describing a conductivity component, with the one or more processors, calculating from the imaginary part of the conductivity component a conductivity distribution, with the one or more processors, from the the conductivity distribution, constructing a specific absorption rate (SAR) map.

8. A non-transitory, tangible computer-readable medium carrying computer executable instructions to perform the method as claimed in claim 1.

9. A magnetic resonance system for performing electric properties tomography imaging of an object, the system including at least one processor configured for:

controlling radio frequency and gradient coils to apply an imaging sequence that includes an excitation RF field to the object via a coil at a first spatial coil position, acquiring resulting magnetic resonance signals via a receiving channel from the object, determining from the acquired magnetic resonance signals a first phase distribution and a first amplitude of a first magnetic field component of the excitation RF field of the coil at the first coil position, controlling the radio frequency and gradient coils to apply an excitation RF field to the object via a coil at a second spatial coil position, wherein the second spatial coil position is different from the first spatial coil position, acquiring resulting magnetic resonance signals via the receiving channel from the object, determining from the acquired magnetic resonance signals a second phase distribution and a second amplitude of a second magnetic field component of the excitation RF field of the coil at the second coil position, determining a phase difference distribution between the first and second phase distributions, determining from the first and second phase distributions, a first complex permittivity expression as a function of the first amplitude of the first magnetic field component and a second complex permittivity expression as a function of the second amplitude of the second magnetic field component and the phase difference, from the first complex permittivity expression and the second complex permittivity expression, determining a specific absorption ratio map.

10. A magnetic resonance system for performing electric properties tomography imaging of an object, the system being arranged for:

applying an excitation RF field to the object via a first coil at a first coil position and acquiring resulting magnetic resonance signals via a receiving channel from the object, with a processor, determining from the acquired magnetic resonance signals a first magnetic field component of the excitation RF field of the coil at the first coil position, the first magnetic field component including a first amplitude distribution and a first phase distribution, applying an excitation RF field to the object via a second coil at a second coil position and acquiring resulting magnetic resonance signals via a receiving channel from the object, wherein the first coil position is different from the second coil position, with a processor, determining from the acquired magnetic resonance signals a second magnetic field component of the excitation RF field of the coil at the second coil position, the second magnetic field component including a second amplitude distribution and a second phase distribution, with the processor, determining a phase difference distribution between the first and second phase distributions, with the processor, calculating a complex permittivity using the phase difference distribution, with the processor, splitting said complex permittivity into a real part describing a permittivity distribution and an imaginary part describing a conductivity distribution, with the processor, from the conductivity distribution, constructing a specific absorption rate (SAR) map.

11. The magnetic resonance system of claim 10, further including:

with the processor, segmenting a magnetic resonance image of the object based on the specific absorption ratio map.

* * * * *